United States Patent
Nakashimada et al.

(10) Patent No.: US 9,181,557 B2
(45) Date of Patent: Nov. 10, 2015

(54) URACIL-REQUIRING MOORELLA BACTERIA AND TRANSFORMING-GENE-INTRODUCED MOORELLA BACTERIA

(75) Inventors: Yutaka Nakashimada, Hiroshima (JP); Akihisa Kita, Hiroshima (JP); Tohru Suzuki, Gifu (JP); Shinsuke Sakai, Chiba (JP); Kazue Takaoka, Tokyo (JP)

(73) Assignees: Mitsui Engineering & Shipbuilding Co., Ltd., Tokyo (JP); Hiroshima University, Hiroshima (JP); Gifu University, Gifu (JP)

( * ) Notice: Subject to any disclaimer, the term of this patent is extended or adjusted under 35 U.S.C. 154(b) by 0 days.

(21) Appl. No.: 14/123,301

(22) PCT Filed: Jun. 1, 2012

(86) PCT No.: PCT/JP2012/064306
§ 371 (c)(1),
(2), (4) Date: Mar. 24, 2014

(87) PCT Pub. No.: WO2012/165626
PCT Pub. Date: Dec. 6, 2012

(65) Prior Publication Data
US 2014/0206065 A1    Jul. 24, 2014

(30) Foreign Application Priority Data
Jun. 2, 2011 (JP) .................. 2011-124458

(51) Int. Cl.
C12N 1/21 (2006.01)
C12N 15/74 (2006.01)
C12N 9/88 (2006.01)
C12P 7/06 (2006.01)

(52) U.S. Cl.
CPC .................. *C12N 15/74* (2013.01); *C12N 9/88* (2013.01); *C12P 7/065* (2013.01); *C12Y 401/01023* (2013.01); *C12N 2510/00* (2013.01); *C12N 2510/02* (2013.01); *Y02E 50/17* (2013.01)

(58) Field of Classification Search
None
See application file for complete search history.

(56) References Cited

FOREIGN PATENT DOCUMENTS

JP    201017131    1/2010

*Primary Examiner* — Suzanne M Noakes
*Assistant Examiner* — Jae W Lee
(74) *Attorney, Agent, or Firm* — K. David Crockett, Esq.; Niky Economy Syrengelas, Esq.; Crockett & Crockett, PC (57) ABSTRACT

The present invention provides uracil-requiring *Moorella* bacteria obtained by destroying a gene coding for orotidine-5-phosphate decarboxylase; and transforming-gene-introduced *Moorella* bacteria obtained by introducing a gene coding for orotidine-5-phosphate decarboxylase and a transforming-gene to a chromosome of the uracil-requiring *Moorella* bacteria. The present invention was accomplished by uracil-requiring *Moorella* bacteria, comprising an MTA-D-pF strain that is obtained by destroying a gene coding for orotidine-5-phosphate decarboxylase on a chromosome of *Moorella* bacteria.

2 Claims, 4 Drawing Sheets

CGGGTTTAACCTCAAACCCCTGCAGGAGTATGTACCCCTTTCCCGT
CCTTAACGGAGGAGCGCCAAATCGCCTCCGCCCCACCCCGGCAGG
AGCAGCAGCCCGCGGCTGCACCGGCCGGGCGGTTTCCCGGCCGG
CCCTTCAAGCACCAGGCGAGATGGCCGGGCCGCCGCCATTTAGCA
TATCAAGAGCGCCGGAAGGGAAGGGCTTTTCCGGTTTTTACCGGTC
GGGGTTAAGCCTGACTTAAGGGCCGGTACCGGACCCTCCCCATAT
TCACTCCGCTTACACTCCGTTTTTTGAACTATAAGATCATAAAGCGA
TATTTAAGGGCTTCTGGCCTGCTTGCCAACACTAATGTACCT
START CODON

SEQUENCE LISTING

<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<223> OTHER INFORMATION: PRIMER

<400> SEQUENCE: 1
tgacgttcta gaccctacct ctccaagatt acc                33

<210> SEQ ID NO 2
<211> LENGTH: 29
<212> TYPE: DNA
<213> ORGANISM: Artificial Sequence
<220> FEATURE:
<223> OTHER INFORMATION: PRIMER

<400> SEQUENCE: 2
tgacgtacta gtggcaagca ggccagaag                     29

<210> SEQ ID NO 3
<211> LENGTH: 33
<212> TYPE: DNA
<213> ORGANISM: Artificial Sequence
<220> FEATURE:
<223> OTHER INFORMATION: PRIMER

<400> SEQUENCE: 3

-continued tgacgtacta gtaacttcgg cctgctttca tgc                      33

<210> SEQ ID NO 4
<211> LENGTH: 34
<212> TYPE: DNA
<213> ORGANISM: Artificial Sequence
<220> FEATURE:
<223> OTHER INFORMATION: PRIMER

<400> SEQUENCE: 4
tgacctgata tctgtccaag cttatgcacc ttcc                     34

<210> SEQ ID NO 5
<211> LENGTH: 22
<212> TYPE: DNA
<213> ORGANISM: Artificial Sequence
<220> FEATURE:
<223> OTHER INFORMATION: PRIMER

<400> SEQUENCE: 5
accctacctc tccaagatta cc                                  22

<210> SEQ ID NO 6
<211> LENGTH: 22
<212> TYPE: DNA
<213> ORGANISM: Artificial Sequence
<220> FEATURE:
<223> OTHER INFORMATION: PRIMER

<400> SEQUENCE: 6
tgtccaagct tatgcacctt cc                                  22

<210> SEQ ID NO 7
<211> LENGTH: 19
<212> TYPE: DNA
<213> ORGANISM: Artificial Sequence
<220> FEATURE:
<223> OTHER INFORMATION: PRIMER

<400> SEQUENCE: 7
tgtcctcaac accctcacc                                      19

<210> SEQ ID NO 8
<211> LENGTH: 19
<212> TYPE: DNA
<213> ORGANISM: Artificial Sequence
<220> FEATURE:
<223> OTHER INFORMATION: PRIMER

<400> SEQUENCE: 8
tcttcccagg tcctgtagg                                      19

<210> SEQ ID NO 9
<211> LENGTH: 21
<212> TYPE: DNA
<213> ORGANISM: Artificial Sequence
<220> FEATURE:
<223> OTHER INFORMATION: PRIMER

<400> SEQUENCE: 9
acctgaagtt ccacgacatc c                                   21

<210> SEQ ID NO 10
<211> LENGTH: 18
<212> TYPE: DNA

```
<213> ORGANISM: Artificial Sequence
<220> FEATURE:
<223> OTHER INFORMATION: PRIMER

<400> SEQUENCE: 10
ggtcacgatg acgaactc                                                    18

<210> SEQ ID NO 11
<211> LENGTH: 35
<212> TYPE: DNA
<213> ORGANISM: Artificial Sequence
<220> FEATURE:
<223> OTHER INFORMATION: PRIMER

<400> SEQUENCE: 11
agactaacaa cttcaagggg tacatactcc tgcag                                 35

<210> SEQ ID NO 12
<211> LENGTH: 33
<212> TYPE: DNA
<213> ORGANISM: Artificial Sequence
<220> FEATURE:
<223> OTHER INFORMATION: PRIMER

<400> SEQUENCE: 12
cagtggttac tgacatcccg tccttaacgg agg                                   33

<210> SEQ ID NO 13
<211> LENGTH: 33
<212> TYPE: DNA
<213> ORGANISM: Artificial Sequence
<220> FEATURE:
<223> OTHER INFORMATION: PRIMER

<400> SEQUENCE: 13
agactaacaa cttcagctcc tccgttaagg acg                                   33

<210> SEQ ID NO 14
<211> LENGTH: 33
<212> TYPE: DNA
<213> ORGANISM: Artificial Sequence
<220> FEATURE:
<223> OTHER INFORMATION: PRIMER

<400> SEQUENCE: 14
cagtggttac tgacacttca agcaccaggc gag                                   33

<210> SEQ ID NO 15
<211> LENGTH: 33
<212> TYPE: DNA
<213> ORGANISM: Artificial Sequence
<220> FEATURE:
<223> OTHER INFORMATION: PRIMER

<400> SEQUENCE: 15
agactaacaa cttcactcgc ctggtgcttg aag                                   33

<210> SEQ ID NO 16
<211> LENGTH: 34
<212> TYPE: DNA
<213> ORGANISM: Artificial Sequence
<220> FEATURE:
<223> OTHER INFORMATION: PRIMER

<400> SEQUENCE: 16
cagtggttac tgacaggaag ggaagggctt ttcc                                  34
```

```
<210> SEQ ID NO 17
<211> LENGTH: 24
<212> TYPE: DNA
<213> ORGANISM: Artificial Sequence
<220> FEATURE:
<223> OTHER INFORMATION: PRIMER

<400> SEQUENCE: 17
tgaagttgtt agtcttcctc atgc                                              24

<210> SEQ ID NO 18
<211> LENGTH: 22
<212> TYPE: DNA
<213> ORGANISM: Artificial Sequence
<220> FEATURE:
<223> OTHER INFORMATION: PRIMER

<400> SEQUENCE: 18
gtcagtaacc actgatgaac ac                                                22

<210> SEQ ID NO 19
<211> LENGTH: 360
<212> TYPE: DNA
<213> ORGANISM: Thermoanaerobacter ethanolicus 39E

<400> SEQUENCE: 19
cgggtttaac ctcaaacccc tgcaggagta tgtaccccctt tcccgtcctt aacggaggag       60
cgccaaatcg cctccgcccc accccggcag gagcagcagc ccgcggctgc accggccggg      120
cggtttcccg gccggccctt caagcaccag gcgagatggc cgggccgccg ccatttagca      180
tatcaagagc gccggaaggg aagggcttt ccggttttta ccggtcgggg ttaagcctga       240
cttaagggcc ggtaccggac cctccccata ttcactccgc ttacactccg tttttttgaac    300 tataagatca taaagcgata tttaagggct tctggcctgc ttgccaacac taatgtacct     360
```

URACIL-REQUIRING MOORELLA BACTERIA AND TRANSFORMING-GENE-INTRODUCED MOORELLA BACTERIA

The present application incorporates by reference the contents of the ASCII compliant file in their entirety into the present application. The sequence listing contained on the ASCII compliant file is entitled 213-644US_SEQUENCE_LISTING.txt. The ASCII compliant file was created on Dec. 1, 2013 and is 2 KB.

TECHNICAL FIELD

A substitute sequence Listing, entitled 213-644US_SEQUENCE_LISTING_AMENDED3.txt, is provided electronically and is incorporated by reference in its entirety. The electronic file was created Jun. 10, 2015 and is 3 KB in size.

The present invention relates to uracil-requiring *Moorella* bacteria and transforming-gene-introduced *Moorella* bacteria, particularly to uracil-requiring *Moorella* bacteria obtained by destroying a gene coding for orotidine-5-phosphate decarboxylase and transforming-gene-introduced *Moorella* bacteria obtained by introducing a gene coding for orotidine-5-phosphate decarboxylase and a transforming-gene to a chromosome of the uracil-requiring *Moorella* bacteria.

BACKGROUND ART

*Moorella* bacteria, which are industrially advantageous in producing acetic acid and ethanol from a gas, are expected to show improvement in production efficiency for e.g. ethanol.

Inventors of the present invention examined introduction of a useful function such as improvement in production efficiency for ethanol by transforming *Moorella* bacteria. However, since *Moorella* bacteria are genetically specific unlike other types of bacteria and have not been fully identified in property, it is, in fact, technologically difficult to transform *Moorella* bacteria. In cases where a mutation treatment is performed on *Moorella* bacteria with a chemical substance such as nitrosoguanidine (NTG), a strain that can maintain ethanol production in large volumes even after several passages cannot be obtained, or a transformation-confirmed strain was not obtained when a plasmid vector as an extrachromosomal gene was attempted to be introduced.

Inventors of the present invention have experimentally succeeded in obtaining uracil-requiring *Moorella* bacteria by destroying a gene coding for orotate phosphoribosyltransferase (pyrE) as an enzyme associated with a uracil biosynthetic system by homologous recombination by using a *Moorella* sp. HUC22-1 strain (*Moorella* bacteria) as a basal strain (Patent Document 1).

However, since the uracil-requiring *Moorella* bacteria had a difficulty in completing complementary sequence by incorporating a pyrE again, a specific method for expressing a transforming-gene by introducing the transforming-gene was unsuccessfully established.

PRIOR ART DOCUMENT

Patent Document

Patent Document 1: JP-A-2010-17131

SUMMARY OF THE INVENTION

Problems to be Solved by the Invention

Inventors of the present invention carried out extended research, in order to establish a process for expressing a transforming-gene in *Moorella* bacteria by homologous recombination, obtain new uracil-requiring *Moorella* bacteria by destroying a gene coding for orotidine-5-phosphate decarboxylase (pyrF) and find out a specific method for expressing a transforming-gene by introducing a pyrF and a transforming-gene to a chromosome of the uracil-requiring *Moorella* bacteria to complete the present invention.

Accordingly, the present invention provides uracil-requiring *Moorella* bacteria obtained by destroying a gene coding for orotidine-5-phosphate decarboxylase, and transforming-gene-introduced *Moorella* bacteria obtained by introducing a gene coding for orotidine-5-phosphate decarboxylase and a transforming-gene to a chromosome of the uracil-requiring *Moorella* bacteria.

Another problem of the present invention is obviously described as follows.

Means for Solving the Problem

The above problems are solved by each of the following inventions.

Uracil-requiring *Moorella* bacteria, comprising an MTA-D-pF strain that is obtained by destroying a gene coding for orotidine-5-phosphate decarboxylase on a chromosome in *Moorella* bacteria.

Transforming-gene-introduced *Moorella* bacteria obtained by introducing a gene coding for orotidine-5-phosphate decarboxylase and a transforming-gene to a chromosome of the uracil-requiring *Moorella* bacteria according to 1 by homologous recombination.

Advantageous Effect of the Invention

The present invention can provide uracil-requiring *Moorella* bacteria obtained by destroying a gene coding for orotidine-5-phosphate decarboxylase, and transforming-gene-introduced *Moorella* bacteria obtained by introducing a gene coding for orotidine-5-phosphate decarboxylase and a transforming-gene to a chromosome of the uracil-requiring *Moorella* bacteria.

BEST MODE FOR CARRYING OUT THE INVENTION

The present invention will be described as follows.

The uracil-requiring *Moorella* bacteria and the transforming-gene-introduced *Moorella* bacteria according to the present invention can be used for a process for expressing a transforming-gene in *Moorella* bacteria.

The uracil-requiring *Moorella* bacteria according to the present invention is obtained by destroying a gene coding for orotidine-5-phosphate decarboxylase on a chromosome in *Moorella thermoacetica* ATCC 39073 strain as a basal strain, and is under national deposit of NITE Patent Microorganisms Depositary (NPMD) Address: #120, 2-5-8 Kazusakamatari, Kisarazu-shi, Chiba 292-0818, Japan) as an MTA-D-pF strain (accession number: NITE BP-1057). The national deposit will be transferred to international deposit as of Jun. 1, 2012 and NPMD issues the certification "Notice of acceptance of biological genetic resources" as of this date. The international deposit accession number will be NITE BP-1057.

Uracil requiring property means a property of a strain to require uracil for growth as a source of nutrition. Since *Moorella* bacteria can normally biosynthesize uracil, it has no uracil requiring property. However, in case of mutation that fails to biosynthesize uracil, uracil is required to be produced. A uracil requiring strain is a strain having this type of uracil requiring property.

An orotidine-5-phosphate decarboxylase is an enzyme involved in biosynthesizing UMP (uridine phosphate) as a precursor of a pyrimidine base required for biosynthesizing uracil. Lack of a gene coding therefore leads to an inability to biosynthesize UMP, resulting in expression of uracil requiring property.

The cultural properties of the uracil-requiring *Moorella* bacteria according to the present invention are as follows. A circular colony 3 to 5 mm in diameter is formed in a modified ATCC 1754 PETC agar medium (*1) on an anaerobic condition at 55° C. for 3 to 5 days.
 i) Color: brown
 ii) Surface shape: smooth
 iii) Transparency: opaque
*1 Modified ATCC 1754 PETC agar medium

| | |
|---|---|
| NH$_4$Cl | 1.0 g |
| KCl | 0.1 g |
| MgSO$_4$ | 0.2 g |
| NaCl | 0.8 g |
| KH$_2$PO$_4$ | 0.1 g |
| CaCl$_2$ | 0.02 g |
| Yeast Extract | 1.0 g |
| Uracil (No Yeast Extract added) | 0.01 g |
| NaHCO$_3$ | 2.0 g |
| Cysteine-HCl | 0.3 g |
| Trace element solution (I) | 10 ml |
| Vitamin solution (II) | 10 ml |
| Distilled water | 1000 ml |
| Agar (at high temperature) | 20 g |
| Fructose | 5.0 g |
| pH 5.9 (prior to sterilization) | |

Sterilization temperature and time: 121° C., 15 min.
The compositions of the above (I) Trace element solution and (II) Vitamin solution are as follows.
(I) Trace Element Solution

| | |
|---|---|
| Nitrolotriacetic acid | 2.0 g |
| MnSO$_4$·H$_2$O | 1.0 g |
| Fe(SO$_4$)$_2$(NH$_4$)$_2$·6H$_2$O | 0.8 g |
| CoCl$_2$·6H$_2$O | 0.2 g |
| ZnSO$_4$·7H$_2$O | 0.0002 g |
| CuCl$_2$·2H$_2$O | 0.02 g |
| NiCl$_2$·6H$_2$O | 0.02 g |
| Na$_2$MlO$_4$·2H$_2$O | 0.02 g |
| Na$_2$SeO$_4$ | 0.02 g |
| Na$_2$WO$_4$ | 0.02 g |
| Distilled water | 1000 ml |

(II) Vitamin Solution

| | |
|---|---|
| Biotin | 2.0 mg |
| Folic acid | 2.0 mg |
| Pyridoxine-HCl | 10 mg |
| Thiamine-HCl | 5.0 mg |
| Riboflavin | 5.0 mg |
| Nicotinic acid | 5.0 mg |
| D-Ca-pantothenate | 5.0 mg |
| Vitamin B$_{12}$ | 0.1 mg |
| p-Aminobenzoic acid | 5.0 mg |
| Thioctic acid | 5.0 mg |
| Distilled water | 1000 ml |

The uracil-requiring *Moorella* bacteria according to the present invention have an ability to produce ethanol from hydrogen and carbon dioxide or carbon monoxide due to a trait preferably taken over from a *Moorella thermoacetica* ATCC 39073 strain as a basal strain. Thus, the uracil-requiring *Moorella* bacteria are preferably used to create a strain having a high ethanol production efficiency by introducing a transforming-gene.

The uracil-requiring *Moorella* bacteria according to the present invention can be obtained by destroying a gene coding for orotidine-5-phosphate decarboxylase on a chromosome by homologous recombination by using a primer set represented by SEQ ID No. 1 to 4 in a *Moorella thermoacetica* ATCC 39073 strain as a basal strain.

A method for creating the uracil-requiring *Moorella* bacteria according to the present invention will be described in detail.

A primer set represented by SEQ ID No. 1 to 4 in the present invention is used for homologous recombination that imparts a uracil requiring property by destroying a gene coding for orotidine-5-phosphate decarboxylase (hereinafter referred to as pyrF) in a *Moorella thermoacetica* ATCC 39073 strain as a basal strain.

Specifically, a primer set represented by SEQ ID No. 1 and 2 amplifies an upstream region adjacent to a pyrF on a chromosome of *Moorella* bacteria.

Meanwhile, a primer set represented by SEQ ID No. 3 and 4 amplifies a downstream region adjacent to a pyrF on a chromosome of *Moorella* bacteria.

By ligating a PCR product obtained by PCR by using a primer set represented by SEQ ID No. 1 and 2 and each PCR product obtained by PCR by using a primer set represented by SEQ ID No. 3 and 4, a DNA fragment in which a pyrF is deleted or destroyed and an upstream region and a downstream region adjacent to the pyrF are contained is obtained.

A DNA fragment obtained is incorporated into a plasmid to construct a plasmid for destroying a pyrF, and introduced to a *Moorella thermoacetica* ATCC 39073 strain as a basal strain. Accordingly, homologous recombination is induced on the *Moorella thermoacetica* ATCC 39073 strain and a pyrF is destroyed in a gene on a chromosome.

In the present invention, a method for introducing a plasmid for destroying a pyrF to a *Moorella thermoacetica* ATCC 39073 strain as a basal strain is not particularly restricted, and preferably by means of e.g. electroporation.

In the above manner, the uracil-requiring *Moorella* bacteria according to the present invention are obtained by destroying a pyrF by homologous recombination.

Destruction of the pyrF gene can be confirmed by PCR by using a genome DNA of the *Moorella thermoacetica* ATCC 39073 strain as a basal strain and a genome DNA of the uracil-requiring *Moorella* bacteria obtained each as a template.

A primer represented by SEQ ID No. 5 to 10 can preferably be used when PCR confirms if a pyrF in a created cell is deleted or destroyed.

In a pyrF-destroying strain obtained, a possibility of eliminating a uracil requiring property by introducing a pyrF gene and restoring a lost pyrimidine biosynthetic pathway, i.e. completing complementary sequence can be confirmed.

In order to confirm a complementary sequence, a gene coding for orotidine-5-phosphate decarboxylase on a chromosome in *Moorella* bacteria and an upstream region and a downstream region adjacent to the same are first amplified by using a primer represented by SEQ ID No. 1 and/or 4.

Subsequently, a DNA fragment amplified is incorporated into a plasmid to construct a plasmid for confirming a complementary sequence having a pyrF between homologous sites composed of an upstream region and a downstream region.

If a plasmid for confirming a complementary sequence is introduced to a pyrF-destroying strain to confirm bacteria growth in a uracil-defective medium, it is confirmed that the pyrF-destroying strain can be in the form of complementary sequence.

The uracil-requiring *Moorella* bacteria obtained according to the present invention can preferably be used as a transforming basal strain that introduces a gene imparting a specific function such as improvement in ethanol productivity with reference to identified homologous sites and destroying-gene.

For instance, a vector for introducing a transforming-gene having a pyrF gene between 2 homologous sites and a transforming-gene to be introduced (gene that imparts a specific function) is prepared. Introduction of the same to a pyrF-destroying strain restores a pyrimidine biosynthetic pathway and eliminates a uracil requiring property, thereby forming *Moorella* bacteria that can express a specific transforming-gene. By isolating bacteria according to a uracil requiring property such as isolating bacteria that can grow in a uracil-defective medium, a transforming-gene is introduced to readily obtain a transforming strain that is imparted with a specific function.

In order to create a vector for introducing a transforming-gene, a primer set represented by SEQ ID No. 1 and 4 can preferably be used.

More specifically, a primer set represented by SEQ ID No. 1 and 4 amplifies a gene coding for orotidine-5-phosphate decarboxylase on a chromosome in *Moorella* bacteria and both regions adjacent to an upstream region and a downstream region.

By using a primer set represented by SEQ ID No. 1 and 4, a transforming-gene is incorporated into an upstream region or a downstream region of a pyrF in a DNA fragment amplified with a chromosome in *Moorella* as a template to prepare a DNA fragment in which a pyrF and a transforming-gene are present between both regions adjacent to the upstream region and the downstream region.

By incorporating a DNA fragment prepared into a plasmid, a vector for introducing a transforming-gene can be constructed.

In the present invention, a transforming-gene may be a gene that is originally found in *Moorella* bacteria, in addition to a gene that is not originally found in *Moorella* bacteria. More specifically, it is preferable that a gene that is originally found in *Moorella* bacteria be additionally incorporated in order to increase the number of genes retained (i.e. to promote expression).

By introducing a vector for introducing a transforming-gene to a pyrF-destroying strain, homologous recombination is induced to incorporate a pyrF and a transforming-gene into a chromosome of a pyrF-destroying strain.

In the above manner, transforming-gene-introduced *Moorella* bacteria obtained by introducing a transforming-gene by homologous recombination are obtained on a chromosome of a pyrF-destroying strain.

The transforming-gene-introduced Moorella bacteria can retain a transforming-gene on a chromosome so as to be expressed.

EXAMPLE

Example 1

The following media used for preparing *Moorella* bacteria and reagents are all prepared on an anaerobic and sterile condition and procedures are performed in an anaerobic environment.

1. Preparation of pyrF Gene-Destroying Strain (ΔpyrF Strain) of *Moorella Thermoacetica* ATCC 39073 Strain 1.1. Construction of pyrF Gene-Destroying-Vector A vector for destroying an orotidine-5'-phosphate decarboxylase gene pyrF of a *Moorella thermoacetica* ATCC 39073 strain was constructed according to the following procedures.

[Construction of pyrF Gene-Destroying-Vector Pk18-dpryF]

First, PCR is performed on the conditions shown in Table 2 to amplify about 1000 bp of upstream and downstream regions of a pyrF gene by using a primer combination: a pyrF-uP-F1 (SEQ ID No. 1) and a pyrF-uP-R1 (SEQ ID No. 2), and a primer combination: a pyrF-dn-F1 (SEQ ID No. 3) and a pyrF-dn-R1 (SEQ ID No. 4) shown in Table 1.

Figure 1:
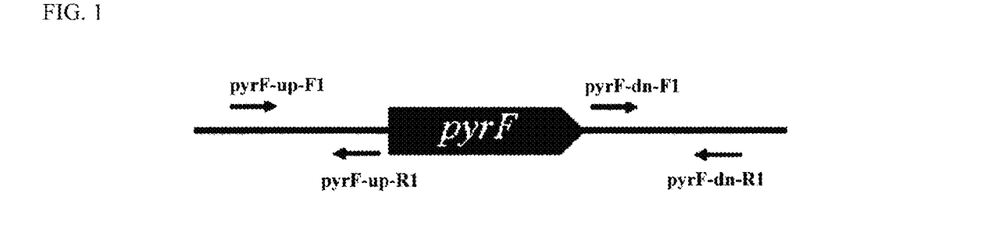
FIG. 1 shows a location of each primer.
Figure 2:
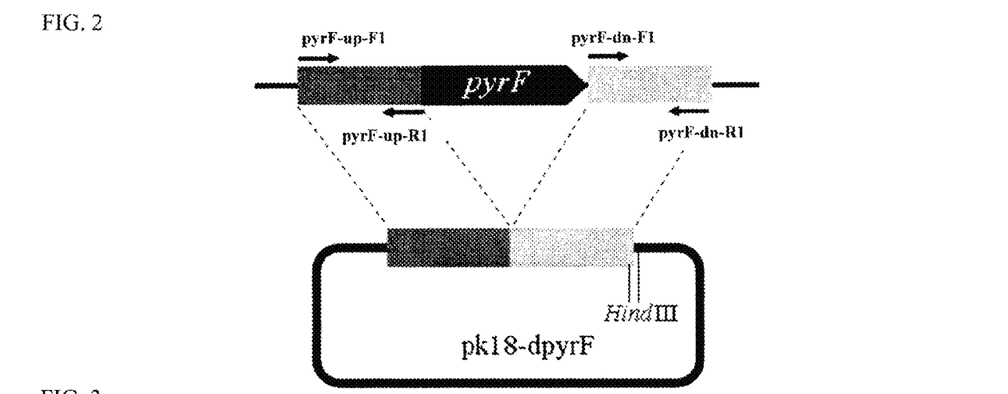
FIG. 2 shows a method for constructing a pyrF gene-destroying-vector pk18-dpryF.

As shown in FIGS. 1 and 2, the primers of the pyrF-uP-F1 (SEQ ID No. 1) and the pyrF-uP-R1 (SEQ ID No. 2) amplify a region adjacent to the upstream region of the pyrF gene, and the primers of the pyrF-dn-F1 (SEQ ID No. 3) and the pyrF-dn-R1 (SEQ ID No. 4) amplify a region adjacent to the downstream region of the pyrF gene.

TABLE 1

Primer used for constructing pyrF gene-destroying vector

| SEQ ID | Name of Primer | Sequence (5' to 3') Supplementary explanation |
|---|---|---|
| No. 1 | pyrF-uP-F1 | Tgacgttctagaccctacctctccaagattacc<br>Restriction enzyme XbaI site added |
| No. 2 | pyrF-uP-R1 | Tgacgtactagtggcaagcaggccagaag<br>Restriction enzyme SpeI site added |
| No. 3 | pyrF-dn-F1 | Tgacgtactagtaacttcggcctgctttcatgc<br>Restriction enzyme SpeI site added |
| No. 4 | pyrF-dn-R1 | Tgacctgatatctgtccaagcttatgcaccttcc<br>Restriction enzyme EcoRV added |

TABLE 2

| KOD-Plus-Neo (Product of TOYOBO Co., Ltd.) | 1 µl | | |
|---|---|---|---|
| 10 × buffer | 5 µl | | |
| 2 mM dNTPs | 5 µl | 94° C. 2 min. | 1 cycle |
| 25 mM MgSO$_4$ | 3 µl | 98° C. 10 sec. | 25 cycle |
| Primer F (10 µM) | 1.5 µl | 55° C. 30 sec. | |
| Primer R (10 µM) | 1.5 µl | 68° C. 45 sec. | |
| Template | 3 µl | 4° C. ∞ | 1 cycle |
| Sterilized water | 30 µl | | |

After a PCR product obtained was treated with a restriction enzyme SpeI, the product was refined using an MagExtractor Kit (Product of TOYOBO Co., Ltd.), 5 µl of a PCR product of a pyrF gene upstream region, 5 µl of a PCR product of a downstream region and 10 µl of Ligation high ver.2 (Product of TOYOBO Co., Ltd.) were mixed and incubated at 16° C. for 30 minutes. By using a ligation product as a template, PCR was performed on the conditions shown in Table 3 by using the primers of the pyrF-uP-F1 (SEQ ID No. 1) and the pyrF-dn-R1 (SEQ ID No. 4).

TABLE 3

| KOD-Plus-Neo (Product of TOYOBO Co., Ltd.) | 1 µl | 94° C. 2 min. | 1 cycle |
|---|---|---|---|
| | | 98° C. 10 sec. | 20 cycle |
| 10 × buffer | 5 µl | 55° C. 30 sec. | |
| 2 mM dNTPs | 5 µl | 68° C. 1 min 15 sec. | |
| 25 mM MgSO$_4$ | 3 µl | 4° C. ∞ | 1 cycle |
| Primer F (10 µM) | 1.5 µl | | |
| Primer R (10 µM) | 1.5 µl | | |
| Template | 2 µl | | |
| Sterilized water | 31 µl | | |

After a PCR product obtained was subjected to gel extraction by using an MagExtractor Kit (Product of TOYOBO Co., Ltd.), 2 µl of a SmaI-treated plasmid pk18mob was mixed with 8 µl of a gel-extracted PCR product and 10 µl of a Ligation high ver.2 (Product of TOYOBO Co., Ltd.) and the product was incubated at 16° C. for one hour. 10 µl of a ligation solution was added to an *Escherichia coli* HST08 Premium competent cell (product of Takara Bio Inc.) to be slowly agitated, allowed to stand in ice water for 10 minutes, subjected to heat shock at 42° C. for 1 minute and was immediately allowed to stand in ice water.

1 ml of an SOC medium was added thereto and the product was incubated at 37° C. for 1 hour. The product was smeared on an LB agar medium (kanamycin, X-Gal, IPTG-containing) and cultured at 37° C. overnight to obtain a grown colony.

[Confirmation of pyrF Gene-Destroying-Vector]

After transplanting the grown colony above (construction of pyrF gene-destroying-vector pk18-dpryF) to a kanamycin-added LB medium, colony direct PCR was performed to confirm an insert. The primers used were a pyrF-uP-F1 (SEQ ID No. 1) and a pyrF-dn-R1 (SEQ ID No. 4) shown in Table 1. Table 4 shows the conditions of the colony direct PCR.

TABLE 4

| Sapphire Amp Master Mix (Product of Takara Bio Inc.) | 10 µl | 94° C. 1 min. | 1 cycle |
|---|---|---|---|
| | | 98° C. 5 sec. | 30 cycle |
| Primer F (10 µM) | 0.5 µl | 55° C. 5 sec. | |
| Primer R (10 µM) | 0.5 µl | 72° C. 30 sec. | |
| Template | colony | 4° C. ∞ | 1 cycle |
| Sterilized water | 9 µl | | |

In a PCR product obtained, a band was confirmed by electrophoresis.

A strain whose band was confirmed was cultured with a kanamycin-added LB liquid medium overnight to extract a plasmid.

After concentration measurement by absorbance and band confirmation by electrophoresis, a base sequence was decoded by sequence to confirm the construction of a targeted pyrF gene-destroying-vector pk18-dpryF.

1.2. Preparation of pyrF Gene-Destroying Strain (ΔpyrF strain) of *M. Thermoacetica* ATCC 39073 Strain The pyrF gene-destroying-vector pk18-dpryF constructed in the above 1.1 was introduced to the *M. thermoacetica* ATCC 39073 strain according to the following procedures, and a strain in which a pyrF gene is destroyed (ΔpyrF strain) by homologous recombination of double cross-over was selected.

[Introduction of pyrF Gene-Destroying-Vector Pk18-dpryF to *M. Thermoacetica* ATCC 39073 Strain]

An HS buffer, composed of 272 mM sucrose and 16 mM HEPES, was prepared using potassium hydroxide so that pH was 7, boiled for 20 minutes and substituted with $N_2$ gas for 20 minutes.

An *M. thermoacetica* ATCC39073 strain was cultured with a modified ATCC 1754 PETC medium with a mixed gas (80% hydrogen and 20% carbon dioxide) as a substrate or a modified ATCC 1754 PETC medium to which glycine was added with a final concentration of 5 g/L.

The *M. thermoacetica* ATCC39073 strain was cultured until the bacterial cell concentration was approx. 0.3 at $OD_{600}$, approx. 100 ml of a culture solution was harvested and a bacterial cell was washed with an HS buffer twice.

The bacterial cell washed was suspended in an approximate amount of a HS buffer (approx. 3 ml) and mixed with 380 µl of a suspension and 20 µl of a plasmid.

Electroporation was performed on a condition of 1.5 kv, 500Ω, 50 µF or 2.0 kv, 500Ω, 50 µF by using a Bio-Rad Gene Pulser (registered trademark) and a cuvette with a gap of 0.2 cm (Product of Bio-Rad Laboratories, Inc.).

A suspension obtained after electroporation was inoculated in 5 ml of a medium to which pyruvic acid was added with a final concentration of 40 mM. 2 days after culturing at 55° C., the product was inoculated in an agar medium to which uracil and 5-fluoroorotic acid (5-FOA) were added with final concentrations of 10 µg/ml and 0.2%, respectively and a roll tube was prepared.

[Confirmation of pyrF Gene-Destroying Strain (ΔpyrF Strain) by Direct PCR]

20 colonies formed in the above agar medium were inoculated in a liquid medium to which 5 ml uracil and 5-FOA were added with final concentrations of 10 µg/ml and 0.2%, respectively, and, 6 strains whose medium was suspended on the $3^{rd}$ day after culturing were selected to harvest 1 ml of a culture solution.

The product was suspended with 20 µl of a TE buffer containing Acromopeptidase (20 mg/ml)+lysozyme (20 mg/ml), incubated at 37° C. for 5 minutes, and 20 µl of DMSO was added thereto and suspended to be defined as a PCR template.

Figure 3:
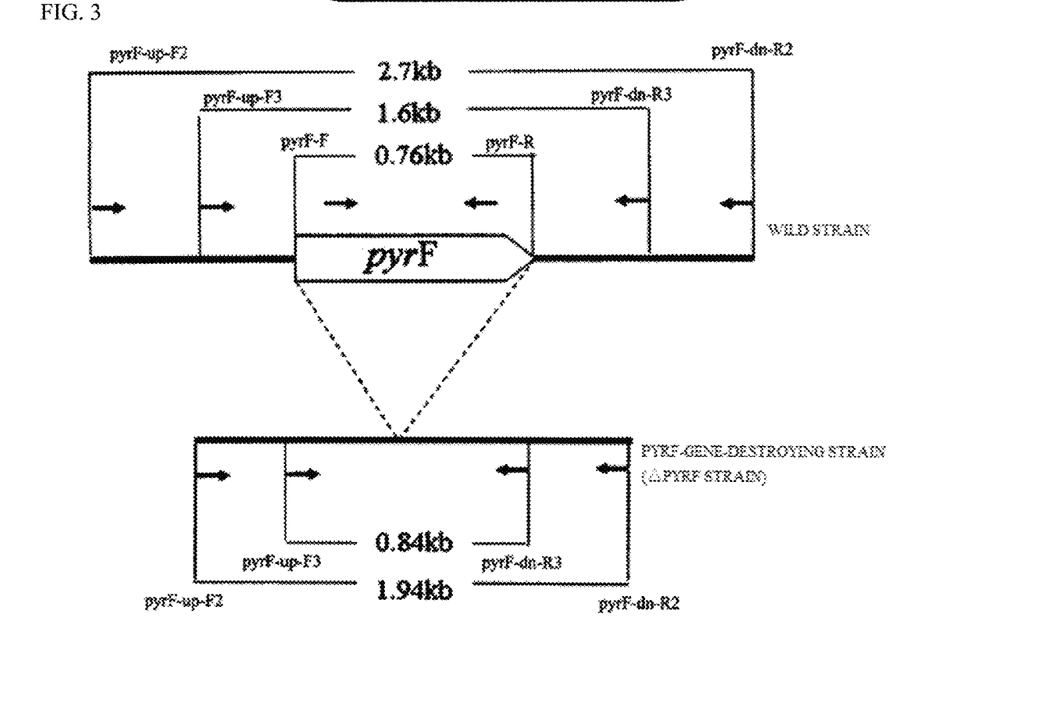
FIG. 3 shows a location of each primer and a length of a DNA fragment.

Colony direct PCR was performed on the conditions shown in Table 6 by using the primer combinations shown in Table 5: a pyrF-uP-F2 (SEQ ID No. 5) and a pyrF-dn-R2 (SEQ ID No. 6), a pyrF-uP-F3 (SEQ ID No. 7) and a pyrF-dn-R3 (SEQ ID No. 8), and a pyrF-F (SEQ ID No. 9) and a pyrF-R (SEQ ID No. 10). A band was confirmed by electrophoresis. FIG. 3 shows the location of each primer and the length of an expected DNA fragment.

TABLE 5

Primer used for confirming pyrF-gene-
destroying strain (ΔpyrF strain)

| SEQ ID No. | Name of Primer | sequence (5' to 3') Supplementary explanation |
|---|---|---|
| 5 | pyrF-up-F2 | accctacctctccaagattacc |
| 6 | pyrF-dn-R2 | tgtccaagcttatgcaccttcc |
| 7 | pyrF-uP-F3 | tgtcctcaacaccctcacc |
| 8 | pyrF-dn-R3 | tcttcccaggtcctgtagg |
| 9 | pyrF-F | acctgaagttccacgacatcc |
| 10 | pyrF-R | ggtcacgatgacgaactc |

TABLE 6

| KOD-FX (Product of TOYOBO Co., Ltd.) | 1 μl | 94° C. 2 min. | 1 cycle |
|---|---|---|---|
| | | 98° C. 10 sec. | 30 cycle |
| 2 × buffer | | 54° C. 30 sec. | |
| dNTPs | 10 μl | 68° C. 3 min. 30 sec. | |
| Primer F (10 μM) | 1.5 μl | 4° C. ∞ | 1 cycle |
| Primer R (10 μM) | 1.5 μl | | |
| Template | 2 μl | | |
| Sterilized water | 10 μl | | |

<Evaluation>

Several attempts to form a colony by roll tube method obtained many colonies. 20 strains were selected therefrom to be cultured in a liquid medium (10 μg/ml uracil and 0.2% 5-FOA). A bacterial cell was harvested from a culture solution in which growth of the bacterial cell was confirmed by direct PCR.

Primer combinations: a pyrF-uP-F2 and a pyrF-do-R2, and a pyrF-uP-F3 and a pyrF-dn-R3 were used in 6 strains that showed proliferation on the 3$^{rd}$ day after culturing. PCR from outside a pyrF found that a band was confirmed shorter than a wild strain in one out of 6 strains.

In addition, a primer combination: a pyrF-F and a pyrF-R was used to perform PC-R inside a pyrF. It found no band in the above strains.

From these observations, it was estimated that strains whose band is shorter than wild strains are likely to correspond to a pyrF gene-destroying strain (ΔpyrF strain), and another PCR was performed after chromosome extraction. As a result, a band pattern which was found like in direct PCR was obtained.

Furthermore, since a pyrF gene-destroyed portion is imparted with one restriction enzyme SpeI site (primer pyrF-up-R1 and pyrF-dn-F1), an SpeI site was cleaved to confirm 2 bands when the above PCR product was treated with SpeI.

Subsequently, a pyrF gene-destroying potential strain was subjected to uracil requiring property test. A pyrF gene-destroying strain was inoculated in a modified ATCC 1754 PETC medium excluding yeast extract, and proliferation was confirmed when uracil was added with a final concentration of 10 μg/ml and was not added.

As a result, bacterial cell proliferation was confirmed in a uracil-added sample on the 2$^{nd}$ day after culturing, while proliferation was not confirmed in a no-uracil-added sample. Consequently, it was confirmed that a pyrF gene is destroyed.

The pyrF gene-destroying strain is under national deposit as an MTA-D-pF strain (accession number: NITEP-1057) at NITE Patent Microorganisms Depositary (NPMD). The national deposit will be transferred to international deposit on Jun. 1, 2012, and NPMD issues the certification "Notice of acceptance of biological genetic resources" as of this date. The international deposit accession number will be NITE BP-1057.

2. Complementarity Test 1 of *M. Thermoacetica* ATCC 39073 pyrF Gene-Destroying Strain (ΔpyrF Strain)

2.1. Construction of pyrF Gene Complementary Vector (Gene-Expression Vector)

A pyrF gene complementary vector was constructed in order to perform a complementarity test of an *M. thermoacetica* ATCC 39073 pyrF gene-destroying strain (ΔpyrF strain) according to the following procedures.

[Construction of pyrF Gene Complementary Vector]

By using a primer combination: a primer pyrF-uP-F1 (SEQ ID No. 1) and a pyrF-dn-R1 (SEQ ID No. 4) shown in Table 1, PCR was perform on conditions shown in Table 7 to amplify a pyrF gene translational region, and approx. 2.7 kbp of a gene fragment containing approx. 1000 bp on 5' side and approx. 1000 bp on 3' side.

TABLE 7

| KOD-FX (Product of TOYOBO Co., Ltd.) | 1 μl | 94° C. 2 min. | 1 cycle |
|---|---|---|---|
| | | 98° C. 10 sec. | 30 cycle |
| 2 × buffer | 25 μl | 54° C. 30 sec. | |
| dNTPs | 10 μl | 68° C. 3 min. 30 sec. | |
| Primer F (10 μM) | 1.5 μl | 4° C. ∞ | 1 cycle |
| Primer R (10 μM) | 1.5 μl | | |
| Template | 2 μl | | |
| Sterilized water | 10 μl | | |

A PCR product obtained was subjected to gel extraction by using MagExtractor Kit (Product of TOYOBO Co., Ltd.).

2 μl of a plasmid pBluescript II KS+ treated with EcoRV or 2 μl of a plasmid pk18mob treated with SmaI were mixed with 8 μl of a gel-extracted PCR product and 10 μl of a Ligation high ver.2 (Product of TOYOBO Co., Ltd.) to be incubated at 16° C. for 1 hour.

10 μl of a ligation solution was added to an *Escherichia coli* HSTO8 Premium competent cell (Product of Takara Bio Inc.) to be lightly agitated, and was allowed to stand in ice water for 10 minutes. Thereafter, the product was subjected to heat shock at 42° C. for 1 minute and immediately allowed to stand in ice water.

1 ml of an SOC medium was added thereto and incubated at 37° C. for 1 hour. When a pBluescript II KS+ is used, the product was smeared in an LB agar medium (ampicillin, X-Gal, IPTG-containing), and when a pk18mob was used, the product was smeared in an LB agar medium (kanamycin, X-Gal, IPTG-containing), and cultured at 37° C. overnight to obtain a grown colony.

[Confirmation of pyrF Gene Complementary Vector]

After the above grown colony was transplanted to an ampicillin- or a kanamycin-added LB agar medium, colony direct PCR was performed to confirm an insert. The primers used were a pyrF-uP-F1 (SEQ ID No. 1) and a pyrF-dn-R1 (SEQ ID No. 4) shown in Table 1. Table 8 shows the conditions of colony direct PCR.

TABLE 8

| KOD-FX (Product of TOYOBO Co., Ltd.) | 1 μl | 94° C. 2 min. | 1 cycle |
|---|---|---|---|
| | | 98° C. 10 sec. | 30 cycle |
| 2 × buffer | 25 μl | 54° C. 30 sec. | |

TABLE 8-continued

| | | | |
|---|---|---|---|
| dNTPs | 10 µl | 68° C. 3 min. 30 sec. | |
| Primer F (10 µM) | 1.5 µl | 4° C. ∞ | 1 cycle |
| Primer R (10 µM) | 1.5 µl | | |
| Template | 2 µl | | |
| Sterilized water | 10 µl | | |

Moreover, a strain in which a band was confirmed by electrophoresis was cultured with an ampicillin-added LB liquid overnight when a pBluescript II KS+ was used, and the strain was cultured with a kanamycin (pk18-epyrF)-added LB liquid overnight when a pk18mob was used to extract a plasmid.

After concentration measurement by absorbance and electrophoresis of an EcoRl- or a Pstl-treated sample, a base sequence was decoded by sequence to confirm the construction of targeted pyrF gene complementary vectors pk18-epyrF and pBS-epyrF.

2.2. Introduction of pyrF Gene Complementary Vector pBS-epyrF to *M. Thermoacetica* ATCC 39073 pyrF Gene-Destroying Strain (ΔpyrF Strain)

The pyrF gene complementary vector pBS-epyrF constructed in 2.1. was introduced to the *M. thermoacetica* ATCC 39073 pyrF gene-destroying strain (ΔpyrF strain) constructed in 1.2. to perform a complementarity test by homologous recombination according to the following procedures.

[Introduction of pyrF Gene Complementary Vector pBS-epyrF by Electroporation]

An HS buffer, composed of 272 mM sucrose and 16 mM HEPES, was prepared using potassium hydroxide so that pH was 6.7, boiled for 20 minutes and substituted with $N_2$ gas for 20 minutes.

A ΔpyrF strain was cultured with a complete synthetic medium to which uracil was added with a final concentration of 10 µg/ml with a mixed gas (80% hydrogen and 20% carbon dioxide) as a substrate.

The strain was cultured until the fungus concentration was approx. 0.1 at $OD_{600}$, approx. 100 ml of a culture solution was harvested and the product was washed with a 272 mM sucrose buffer twice so that pH was 7 using potassium hydroxide.

The bacterial cell washed was suspended in an appropriate amount of an HS buffer (approx. 3 ml) and mixed with 380 µl of a suspension and 20 µl of a plasmid.

Electroporation was performed on a condition of 1.5 kv, 500Ω, 50 µF or 2.0 kv, 500Ω, 50 µF by using a Bio-Rad Gene Pulser (registered trademark) and a cuvette with a gap of 0.2 cm (Product of Bio-Rad Laboratories, Inc.).

A suspension obtained after electroporation was inoculated in 5 ml of a complete synthetic medium to which uracil and pyruvic acid were added with final concentrations of 10 µg/ml and 40 mM, respectively, cultured at 55° C. for 2 days, washed in a complete synthetic medium, inoculated in a medium containing a complete synthetic medium and an agar and a roll tube was prepared.

[Confirmation of pyrF Gene Complementary Strain by Direct PCR]

The colony obtained in the above procedures was inoculated in 5 ml of a complete synthetic medium, samples having a suspended medium on the 4$^{th}$ day after culturing were selected to harvest 1 ml of a culture solution.

The product was suspended with 10 µl of a TE buffer containing Acromopeptidase (20 mg/ml)+lysozyme (20 mg/ml), incubated at 37° C. for 5 minutes, and 10 µl of DMSO was added thereto and suspended to be defined as a PCR template.

Colony direct PCR was performed on the conditions shown in Table 9 by using the primer combination shown in Table 5: a pyrF-uP-F3 (SEQ ID No. 7) and a pyrF-dn-R3 (SEQ ID No. 8).

A band was confirmed by electrophoresis to determine a pyrF gene complementary strain was obtained.

TABLE 9

| | | | |
|---|---|---|---|
| KOD-FX (Product of TOYOBO Co., Ltd.) | 1 µl | 94° C. 2 min. | 1 cycle |
| | | 98° C. 10 sec. | 30 cycle |
| 2 × buffer | 25 µl | 54° C. 30 sec. | |
| dNTPs | 10 µl | 68° C. 2 min. 10 sec. | |
| Primer F (10 µM) | 1.5 µl | 4° C. ∞ | 1 cycle |
| Primer R (10 µM) | 1.5 µl | | |
| Template | 2 µl | | |
| Sterilized water | 10 µl | | |

<Evaluation>

Figure 4:
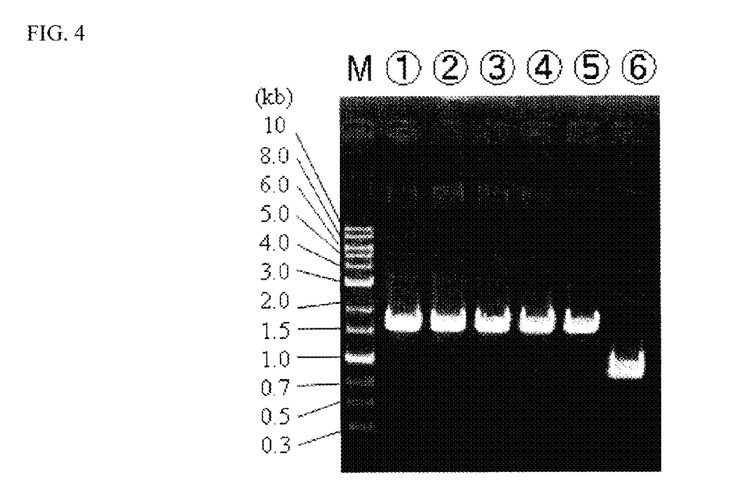
FIG. 4 shows the results of a pyrF complementary potential strain confirmed by direct PCR.

A band in 4 sample strains whose culture solution was white-turbid on the 4$^{th}$ day after culturing was confirmed by direct PCR. FIG. 4 shows the results.

The electrophoresis shown in FIG. 4 found that lanes 1 to 4 correspond to a complementary strain, lane 5 corresponds to a wild strain and lane 6 corresponds to a pyrF-destroying strain. A band was shown in all the 4 strains at the same position of approx. 1.6 kbp as a wild strain. This observation means that a complementary plasmid is incorporated into a cell of a pyrF gene-destroying strain by electroporation and a pyrF is inserted into an original position by homologous recombination. In the pyrF-destroying strain, the length of a band was an expected value at approx. 0.9 bp.

3. Complementarity Test 2 of *M. Thermoacetica* ATCC 39073 pyrF Gene-Destroying Strain (ΔpyrF Strain)

3.1. Construction of Complementary Vector for Inserting Transforming-DNA

When a ΔpyrF strain was subjected to a pyrF gene complementarity test, part of a transforming-gene was inserted into a pyrF upstream region to construct a plasmid whose chromosome can be processed by homologous recombination. Specifically, part of a lacZ gene of a Thermoanaerobacter ethanolicus 39E strain (approx. 500 bp) was inserted into a pyrF gene upstream region of the pyrF gene complementary vector pk18-epyrF constructed in 2.1. The procedures are shown as follows.

[Construction of Complementary Vector for Inserting Transforming-DNA by in-Fusion PCR]

A vector region containing a pyrF gene region was PCR-amplified by using primer combinations: a primer pyrF-1-R (SEQ ID No. 11) and a pyrF-1-F (SEQ ID No. 12), a pyrF-2-R (SEQ ID No. 13) and a pyrF-2-F (SEQ ID No. 14), and a pyrF-3-R (SEQ ID No. 1.5) and a pyrF-3-F (SEQ ID No. 16) shown in Table 10. Table 11 shows PCR conditions for each combination.

TABLE 10

| | | Primer used | |
|---|---|---|---|
| SEQ ID No. | Primer F Primer R | Sequence Sequence | Target Gene |
| 11 | pyrF-1-R | agactaacaacttcaaggggtaca tactcctgcag | |
| 12 | pyrF-1-F | cagtggttactgacatcccgtcct taacggagg | |
| 13 | pyrF-2-R | agactaacaacttcagctcctccg ttaaggacg | |

TABLE 10-continued

Primer used

| SEQ ID No. | Primer F Primer R | Sequence | Target Gene |
|---|---|---|---|
| 14 | pyrF-2-F | cagtggttactgacacttcaagcaccaggcgag | |
| 15 | pyrF-3-R | agactaacaacttcactcgcctggtgcttgaag | |
| 16 | pyrF-3-F | cagtggttactgacaggaagggaagggcttttcc | |
| 17 | lacZ-500-F | tgaagttgttagtcttcctcatgc | lacZ (approx. 500 bp) |
| 18 | lacZ-500-R | gtcagtaaccactgatgaacac | |

TABLE 11

| KOD-FX (Product of TOYOBO Co., Ltd.) | 1 µl | 94° C. 2 min. | 1 cycle |
| | | 98° C. 10 sec. | 30 cycle |
| 2 × buffer | 25 µl | 54° C. 30 sec. | |
| dNTPs | 10 µl | 68° C. 6 min. 40 sec. | |
| Primer F (10 µM) | 1.5 µl | 4° C. ∞ | 1 cycle |
| Primer R (10 µM) | 1.5 µl | | |
| Template | 1 µl | | |
| Sterilized water | 1 µl | | |

A lacZ gene region was PCR-amplified by using a primer LacZ-500-F (SEQ ID No. 17) and a LacZ-500-R (SEQ ID No. 18) shown in Table 10. Table 12 shows the PCR conditions.

TABLE 12

| Prime Star MAX (Product of Takara Bio Inc.) | 50 µl | 94° C. 10 sec. | 1 cycle |
| | | 98° C. 10 sec. | 30 cycle |
| Primer F (10 µM) | 3 µl | 54° C. 10 sec. | |
| Primer R (10 µM) | 3 µl | 72° C. 20 sec. | |
| Template | 1 µl | 4° C. ∞ | 1 cycle |
| Sterilized water | 41 µl | | |

Each PCR product was subjected to gel extraction, and In-Fusion PCR (In-Fusion Advantage PCR Cloning Kit, Product of Takara Bio Inc.) was performed on the conditions shown in Table 13.

TABLE 13

| Plasmid (PCR product) | 2 µl |
| Insert | 4 µl |
| Sterilized water | 1 µl |
| In-Fusion buffer | 2 µl |
| In-Fusion Enzyme | 11 µl |

37° C. for 30 minutes→50° C. for 15 minutes

50 µl of sterilized water was added to an In-Fusion sample to be diluted, and 10 µl of a diluted sample was used for transformation.

Colonies were selected by direct PCR.

<Evaluation>

Figure 5:
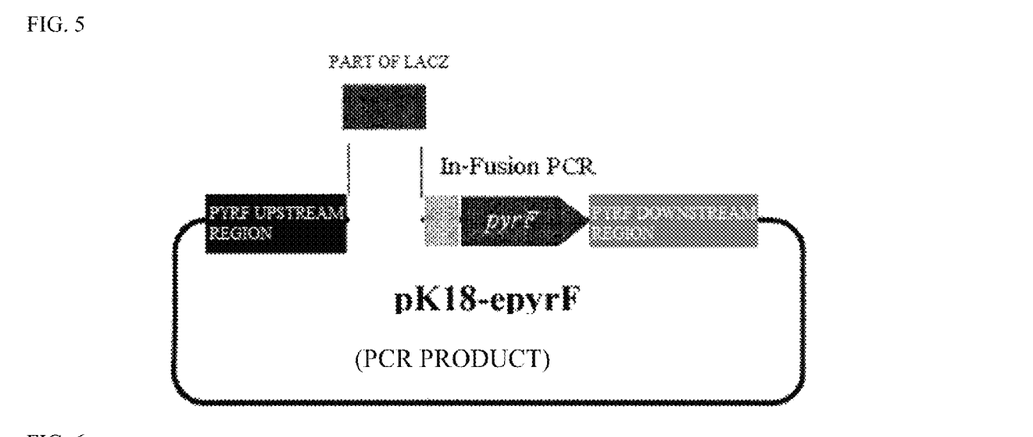
FIG. 5 shows a scheme of a plasmid to be constructed.
Figure 6:
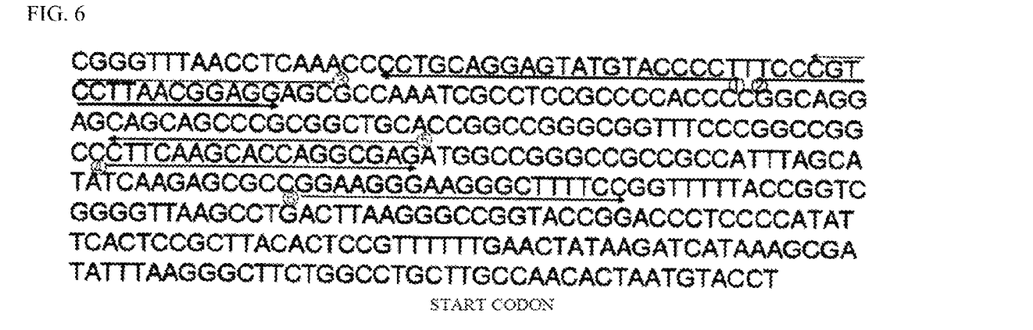
FIG. 6 shows a sequence of a pyrF gene upstream region and a location of a primer.

In order to insert part of a lacZ gene to a pyrF upstream region, inverse PCR was performed by using primer combinations: a primer pyrF-1-R and a pyrF-1-F, pyrF-2-R and a pyrF-2-F, and a pyrF-3-R and a pyrF-3-F with the pk18-epyrF constructed in 2.1. as a template. Accordingly, the position of a primer is shifted so that a promoter region comes at 300 bp, 203 bp, 147 bp to obtain 3 patterns of PCR products (FIGS. 5 and 6). Moreover, in order to insert a lacZ gene to a plasmid by using In-Fusion PCR, a lacZ gene and a homologous sequence were added to each primer. The underlined sequences of SEQ ID No. 11 to 16 in Table 10 correspond to promoter regions. Non-underlined sequences determine the position of a primer, and SEQ ID No. 11 corresponds to a circled number 1 in FIG. 6, SEQ ID No. 12 corresponds to a circled number 2 in FIG. 6, SEQ ID No. 13 corresponds to a circled number 3 in FIG. 6, SEQ ID No. 14 corresponds to a circled number 4 in FIG. 6, SEQ ID No. 15 corresponds to a circled number 5 in FIG. 6 and SEQ ID No. 16 corresponds to a circled number 6 in FIG. 6 (each having arrow).

In-Fusion PCR and transformation in *E. coli* obtained a plurality of colonies. Colony direct PCR with a LacZ-500-F and a LacZ -500-R as a primer found a targeted band in all the strains.

3 strains out thereof were cultured as a group to extract a plasmid. A plasmid composed of primers of a pyrF-1-R and a pyrF-1-F is defined as pk18-pyz-1, a plasmid composed of primers of a pyrF-2-R and a pyrF-2-F is defined as pk18-pyz-2, and a plasmid composed of primers of a pyrF-3-R and a pyrF-3-F is defined as pk18-pyz-3.

Figure 7:
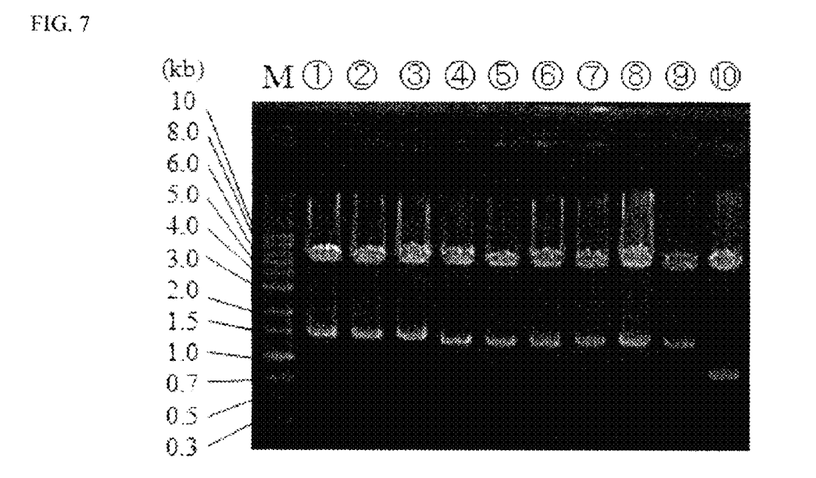
FIG. 7 shows the results confirmed by KpnI treatment.

After confirming a band treated with a restriction enzyme KpnI, an insert of lacZ gene was confirmed in all the strains as shown in FIG. 7.

In electrophoresis observations in FIG. 7, lanes 1, 2 and 3 correspond to a promoter region 300 bp (pk18-pyz-1), lanes 4, 5 and 6 correspond to a promoter region 203 bp (pk18-pyz-2), and lanes 7, 8 and 9 correspond to a promoter region 147 bp (pk18-pyz-3). Lane 10 corresponds to a pk18-epyrF.

3.2. Introduction of Complementary Vector for Inserting Transforming-DNAs Pk18-Pyz-1, Pk18-Pyz-2 and Pk18-Pyz-3 to *M. Thermoacetica* ATCC 39073 pyrF Gene-Destroying Strain (ΔpyrF Strain)

The complementary vectors for inserting a transforming-DNA (pk18-pyz-1, pk18-pyz-2 and pk18-pyz-3) constructed in 3.1. were introduced to the *M. thermoacetica* ATCC 39073 pyrF gene-destroying strain (ΔpyrF strain) constructed in 1.2. according to the following procedures to perform a complementarity test by homologous recombination.

[Introduction of Complementary Vectors for Inserting a Transforming-DNA (Pk18-Pyz-1, Pk18-Pyz-2 and Pk18-Pyz-3) by Electroporation]

An HS buffer, composed of 272 mM sucrose and 16 mM HEPES, was prepared by using potassium hydroxide so that pH was 6.7, boiled for 20 minutes and substituted with $N_2$ gas for 20 minutes.

A ΔpyrF strain was cultured in a complete synthetic medium to which uracil was added with a final concentration of 10 µg/ml with a mixed gas (80% hydrogen and 20% carbon dioxide) as a substrate.

The strain was cultured until the bacterial cell concentration was approx. 0.1 at $OD_{600}$, approx. 50 ml of a culture solution was harvested and the product was washed with a 272 mM sucrose buffer twice so that pH was 7 using potassium hydroxide, and the bacterial cell washed was suspended in an appropriate amount of an HS buffer (approx. 3 ml).

380 µl of a suspension and 5 to 10 µl of a plasmid were mixed and electroporation was performed on a condition of 1.5 kv, 500Ω, 50 µF, or 2.0 kv, 500Ω, 50 µF by using a Bio-Rad Gene Pulser (registered trademark) and a cuvette with a gap of 0.2 cm (Product of Bio-Rad Laboratories, Inc.).

A suspension after electroporation was inoculated in 5 ml of a complete synthetic medium to which uracil was added with a final concentration of 10 µg/ml, cultured with a mixed gas (80% hydrogen and 20% carbon dioxide) as a substrate, cultured at 55° C. for 2 days, washed in a complete synthetic medium, inoculated in a medium containing a complete synthetic medium and an agar and a roll tube was prepared.

[Confirmation of pyrF Gene Complementary Strain by Direct PCR]

The colony obtained in the above procedures was inoculated in 5 ml of a complete synthetic medium, samples having a suspended medium after culturing were selected to harvest 1 ml of a culture solution.

The product was suspended with 10 µl of a TE buffer containing Acromopeptidase (20 mg/ml)+lysozyme (20 mg/ml), incubated at 37° C. for 5 minutes, and 10 µl of a DMSO was added thereto and suspended to be defined as a PCR template.

Colony direct PCR was performed on the conditions shown in Table 14 by using the primer combination shown in Table 5: a pyrF-uP-F3 (SEQ ID No. 7) and a pyrF-dn-R3 (SEQ ID No. 8).

A band was confirmed by electrophoresis to determine a pyrF gene complementary strain was obtained.

TABLE 14

| KOD-FX (Product of TOYOBO Co., Ltd.) | 1 µl | 94° C. 2 min. 98° C. 10 sec. | 1 cycle 30 cycle |
|---|---|---|---|
| 2 × buffer | 25 µl | 54° C. 30 sec. | |
| dNTPs | 10 µl | 68° C. 3 min. 30 sec. | |
| Primer F (10 µM) | 1.5 µl | 4° C. ∞ | 1 cycle |
| Primer R (10 µM) | 1.5 µl | | |
| Template | 2 µl | | |
| Sterilized water | 10 µl | | |

<Evaluation>

Figure 8:
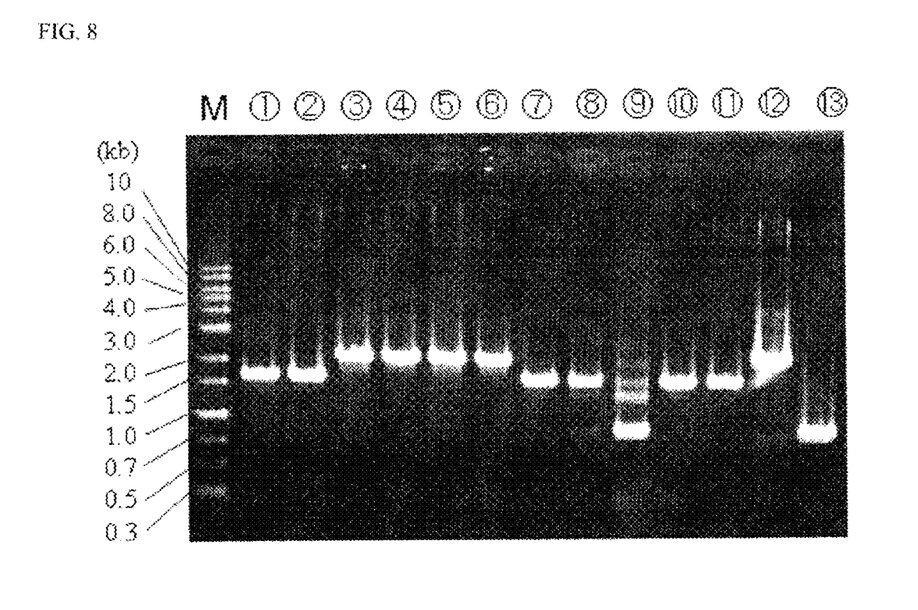
FIG. 8 shows the results of a colony direct PCR.

20 colonies were obtained in total, and 8 strains out thereof were subjected to band confirmation by direct PCR (FIG. 8).

The electrophoresis shown in FIG. 8 found that lanes 1 to 8 correspond to a colony isolated strain, lane 9 corresponds to a ΔpyrF strain direct, lane 10 corresponds to an ATCC39073 wild strain direct, lane 11 corresponds to an extract DNA of an ATCC39073 wild strain, lane 12 corresponds to a complementary vector for inserting a transforming-DNA pk18-pyz-1 and lane 13 corresponds to a pyrF gene-destroying-vector pk18-dpryF.

As shown in FIG. 8, a band was shown in 4 strains (lanes 3, 4, 5 and 6) at the position of approx. 2.1 kbp, bigger than the wild strains (lanes 10 and 11), and introduction of a LacZ gene of approx. 500 bp (transforming-gene) was confirmed. In the remaining 4 strains, a band was shown at the same position of approx. 1.6 kbp as the wild strains.

Figure 9:
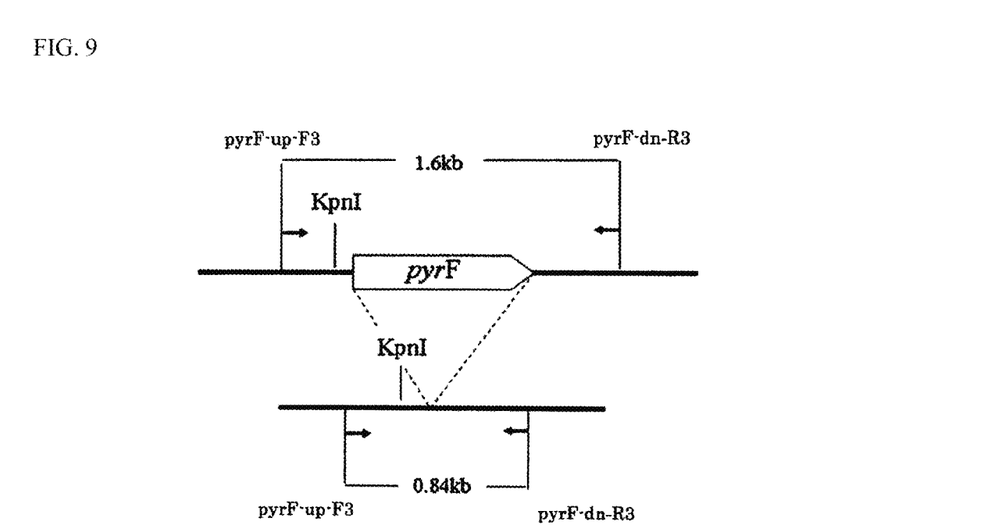
FIG. 9 shows a location of a restriction enzyme KpnI site.
Figure 10:
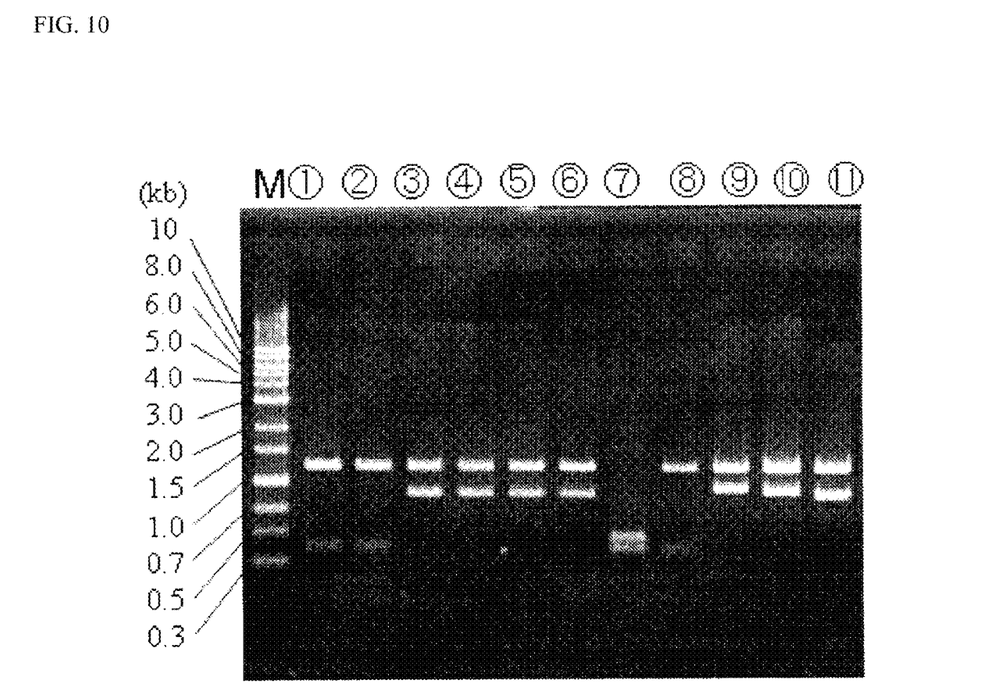
FIG. 10 shows the results of a colony direct PCR product treated with a restriction enzyme KpnI.

Subsequently, PCR products of 6 strains were refined, and treated with a restriction enzyme KpnI confirm a band by electrophoresis. The site of a restriction enzyme KpnI is located at the position in FIG. 9. A PCR product treated with KpnI showed two bands, but a band in a downstream region appeared at the larger position than the wild strains when a transforming-gene was inserted. FIG. 10 shows the results.

In FIG. 10, lanes 1 to 6 correspond to a colony isolated strain, lane 7 corresponds to a ΔpyrF strain direct, lane 8 corresponds to an extract DNA of an ATCC39073 wild strain, lane 9 corresponds to a complementary vector for inserting a transforming-DNA pk18-pyz-1, lane 10 corresponds to a complementary vector for inserting a transforming-DNA pk18-pyz-2 and lane 11 corresponds to a complementary vector for inserting a transforming-DNA pk18-pyz-3.

As shown in FIG. 10, lanes 1 and 2 showed the same band as the wild strains, lanes 3, 4, 5 and 6 showed a band at the larger position than the wild strains, and an insert of a transforming-gene LacZ was confirmed.

In addition, Total DNA was extracted from a bacterial cell obtained not by direct PCR but by proliferation. After PCR on similar conditions confirmed an insert of a transforming-gene LacZ, the results were the same as direct PCR.

The invention claimed is:

1. Uracil-requiring *Moorella* bacteria, consisting of an MTA-D-pF strain with an accession number NITE BP-1057 obtained by destroying a gene coding for orotidine-5-phosphate decarboxylase on a chromosome in *Moorella* bacteria,
    wherein the uracil-requiring *Moorella* bacteria has an ability to express a transforming-gene when a gene coding for orotidine-5-phosphate decarboxylase and the transforming-gene are introduced to a chromosome of the uracil-requiring *Moorella* bacteria by homologous recombination.

2. The uracil-requiring *Moorella* bacteria according to claim 1 obtained by introducing a gene coding for orotidine-5-phosphate decarboxylase and a transforming-gene to a chromosome of the uracil-requiring *Moorella* bacteria by homologous recombination,
    wherein the transforming-gene introduced *Moorella* bacteria has an ability to express the transforming-gene.

* * * * *